United States Patent
Wachtel

(10) Patent No.: US 9,265,910 B2
(45) Date of Patent: Feb. 23, 2016

(54) ADAPTER, INHALATION DEVICE, AND NEBULIZER

(75) Inventor: Herbert Wachtel, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 857 days.

(21) Appl. No.: 13/321,281

(22) PCT Filed: May 5, 2010

(86) PCT No.: PCT/EP2010/002740
§ 371 (c)(1),
(2), (4) Date: Jan. 4, 2012

(87) PCT Pub. No.: WO2010/133294
PCT Pub. Date: Nov. 25, 2010

(65) Prior Publication Data
US 2012/0138049 A1 Jun. 7, 2012

(30) Foreign Application Priority Data
May 18, 2009 (EP) .................................. 09006673

(51) Int. Cl.
*A61M 11/06* (2006.01)
*A61M 16/08* (2006.01)
(Continued)

(52) U.S. Cl.
CPC ......... *A61M 16/0816* (2013.01); *A61M 11/007* (2014.02); *A61M 11/06* (2013.01);
(Continued)

(58) Field of Classification Search
CPC ... A61M 16/125; A61M 11/06; A61M 16/16; A61M 16/0808; A61M 16/0833; A61M 16/208; A61M 15/0065; A61M 15/0086; A61M 16/10; A61M 16/08; A61M 15/0091; A61M 11/00; A61M 15/00; A61M 15/0013–15/0016; A61M 15/002–15/0026; A61M 15/0093–15/0096; A61M 16/00; A61M 16/0816–16/0891; A61M 16/104–16/1045; A61M 16/18–16/209
USPC ............. 128/200.11–200.24, 203.12, 203.15, 128/203.16, 203.17, 203.25, 203.26, 128/203.27, 204.18, 204.21, 205.25, 912, 128/202.27, 207.14; 141/27; 239/338, 352
See application file for complete search history.

(56) References Cited

U.S. PATENT DOCUMENTS 3,580,249 A * 5/1971 Takaoka .................... 128/200.14
4,951,661 A * 8/1990 Sladek ....................... 128/202.27
(Continued)

FOREIGN PATENT DOCUMENTS

CA  2653183 A1  12/2007
CA  2653422 A1  12/2007
(Continued)

OTHER PUBLICATIONS
International Search Report for PCT/EP2010/002740 mailed Nov. 12, 2010.

*Primary Examiner* — Annette Dixon
(74) *Attorney, Agent, or Firm* — Michael P. Morris; Mary-Ellen M. Devlin

(57) ABSTRACT

An adapter includes: a first connection connected to a mouthpiece, a second connection in communication with the first connection, receiving an aerosol, and delivering the aerosol to a patient, a third connection receiving breathable air from a source, a connector located between the first and second connection such that the connector is in fluidic association with an expulsion nozzle of a nebulizer when the first connection is connected to the nebulizer, the connector receiving the aerosol dispensed from the expulsion nozzle and conveying the aerosol to the second connection, where the first connection is connectible in a leak-tight manner to at least one of the expulsion nozzle and a projection that surrounds the expulsion nozzle, so that no supply air or breathable air can flow past the expulsion nozzle through or into the first connection, thereby closing off air supply openings of the nebulizer.

21 Claims, 15 Drawing Sheets

(51) Int. Cl.
*A61M 15/00* (2006.01)
*A61M 11/00* (2006.01)
*A61M 16/12* (2006.01)
*A61M 16/20* (2006.01)
*B05B 11/00* (2006.01)

(52) U.S. Cl.
CPC ....... *A61M15/0013* (2014.02); *A61M 15/0018* (2014.02); *A61M 15/0021* (2014.02); *A61M 15/0065* (2013.01); *A61M 15/0086* (2013.01); *A61M 16/12* (2013.01); *A61M 16/208* (2013.01); *B05B 11/0043* (2013.01); *B05B 11/3001* (2013.01); *B05B 11/309* (2013.01); *B05B 11/3067* (2013.01); *B05B 11/3091* (2013.01)

(56) References Cited

U.S. PATENT DOCUMENTS

| | | | |
|---|---|---|---|
| 5,848,588 A | | 12/1998 | Foley |
| 6,116,233 A | * | 9/2000 | Denyer et al. ............ 128/200.18 |
| 6,363,932 B1 | | 4/2002 | Forchione |
| 6,401,710 B1 | | 6/2002 | Scheuch et al. |
| 6,725,858 B2 | * | 4/2004 | Loescher ................. 128/200.14 |
| 7,556,037 B2 | | 7/2009 | Klein |
| 2001/0035182 A1 | | 11/2001 | Rubin et al. |
| 2002/0046751 A1 | | 4/2002 | MacRae |
| 2003/0098023 A1 | | 5/2003 | Drachmann |
| 2007/0119449 A1 | | 5/2007 | Boehm et al. |
| 2007/0221211 A1 | | 9/2007 | Sagalovich |
| 2009/0314287 A1 | | 12/2009 | Spallek et al. |
| 2012/0138049 A1 | | 6/2012 | Wachtel |

FOREIGN PATENT DOCUMENTS

| | | |
|---|---|---|
| DE | 01102006025871 A1 | 12/2007 |
| EP | 0965355 A2 | 12/1999 |
| EP | 1595564 | 11/2005 |
| EP | 2135632 A1 | 12/2009 |
| JP | 057246 | 2/1993 |
| JP | 05-53470 A | 3/1993 |
| JP | 2004-502502 A | 1/2004 |
| WO | 02/04054 A1 | 1/2002 |
| WO | 03022332 A2 | 3/2003 |
| WO | 03068299 A1 | 8/2003 |
| WO | 2004091704 A1 | 10/2004 |
| WO | 2004098689 A1 | 11/2004 |
| WO | 2007141201 A1 | 12/2007 |
| WO | 2008124666 A2 | 10/2008 |

* cited by examiner

ADAPTER, INHALATION DEVICE, AND NEBULIZER

BACKGROUND

The present invention relates to an adaptor with a first connection for a nebuliser and a second connection on the patient side an inhalation device having a chamber for the intermediate storage of an aerosol, having a first port for connection with a nebuliser that produces the aerosol and a second port on the patient side for delivering the aerosol and with a third port for breathable air and a nebuliser, particularly an inhaler, having such an adaptor or an inhalation device of this kind.

Nebulisers, particularly inhalers, serve to supply a user or patient with an aerosol, i.e. a nebulised fluid, which preferably comprises or contains a medicament or constitutes a medicament preparation. During administration, very precise dosing is often desirable or essential. It is therefore important that a dose dispensed in aerosol form by a nebuliser should be inhaled as completely as possible.

A starting point of the present invention is a nebuliser as described in principle in WO 91/14468 A1 and specifically in WO 97/12687 A1 (FIGS. 6a, 6b). The known nebuliser comprises a pressure generator for conveying and nebulising a medicament preparation. The medicament preparation is delivered in aerosol form through a mouthpiece.

A problem with nebulisers in general is that the triggering of the nebulisation and breathing in have to be co-ordinated. This may be difficult for individual users.

WO 2004/091704 A1 discloses an inhalation device for the intermediate storage of a generated aerosol in a chamber. The known inhalation device is provided for an MDI (Metered Dose Inhaler) and serves to slow down the aerosol, particularly by lengthening the flow path. For this reason, inhalation devices of this kind are also known as spacers. Moreover, the inhalation device serves to store the aerosol produced intermediately so that the user has sufficient time to inhaler the aerosol.

Respiration equipment and systems are used to supply a patient with a breathable gas, generally through at least one gas-carrying tube. In ventilated patients as well, treatment by inhalation may be provided in which an aerosol generated by a nebuliser is introduced into the breathable gas or is breathed-in or inhaled with the breathable gas.

WO 2007/141201 A1 discloses an adaptor having a first connection for a nebuliser and a second connection at the patient end. The known adaptor has a third connection for a breathing tube for supplying a breathing gas. The adaptor is thus designed for connection to a ventilator or ventilating tube. The breathable air supplied through it is conveyed to the first connection of the adaptor and there it is diverted alongside a nozzle of the associated nebuliser protruding into the second connection of the adaptor and together with the aerosol generated by the nebuliser it is expelled through the second connection.

SUMMARY

The aim of the present invention is to provide a simple and/or universally useable adaptor for a nebuliser, an improved inhalation device having a chamber for the intermediate storage of an aerosol produced by a nebuliser, and a nebuliser comprising such an adaptor and/or an inhalation device of this kind.

According to a first aspect of the present invention, an adaptor is provided which has a first connection with an oval cross-section for connecting to an oval mouthpiece of a nebuliser. This provides a very simple means of connection to the associated nebuliser or its mouthpiece.

According to a second aspect of the present invention, an adaptor is provided which comprises a first connection having a connector for accommodating a nozzle of the nebuliser. This is a very simple means of ensuring a good fluidic connection to the associated nebuliser.

According to a third aspect of the present invention an adaptor is provided in which the first connection for the nebuliser and a second connection at the patient end are joined together with no diversions. In particular, the second connection is embodied for connecting to a tube or an inhalation device. This allows for a particularly simple construction and permits particularly universal use of the associated nebuliser together with the adaptor, particularly for attaching to restoration systems or the like. In view of its very simple structure the adaptor is preferably used as a disposable item or is used only once.

According to a fourth aspect of the present invention an inhalation device is provided having a chamber for intermediate storage of an aerosol, wherein the chamber is fluidically connected in valve-free manner on the inlet side to a first port for a nebuliser—at least when the nebuliser is attached—and is connected in parallel on the inlet side via an inlet valve to a port for supplying breathable air, so that breathable air can flow from the latter port through the inlet valve into the chamber. This allows in particular unimpeded or substantially loss-free inflow of aerosol into the chamber, so that the undesirable settling of nebulised fluid on a valve on the inlet side of the chamber can be avoided.

In particular, the chamber is also attached on the outlet side, in valve-free manner, to a patient-side port, so that the aerosol can flow out through the patient-side port largely unimpeded and without loss as it is removed from the chamber.

According to a fifth aspect of the present invention an inhalation device is provided having a chamber for the intermediate storage of aerosol, wherein the chamber comprises on the outlet side a plurality of outlet openings arranged at least substantially in a ring. This surprisingly allows relatively loss-free outflow of the aerosol from the chamber.

According to a sixth aspect of the present invention the adaptor is connected or connectable, more particularly in releasable manner, to an inhalation device having a chamber for the intermediate storage of aerosol. This makes it possible to produce a modular system of simple construction which can be used in highly universal manner. If necessary, the adaptor may also be exchanged or used only once, whereas the inhalation device can be used repeatedly, if necessary.

According to a seventh aspect of the present invention a nebuliser is provided in conjunction with an adaptor as mentioned above and/or an inhalation device as mentioned above. This allows particularly universal use of the nebuliser, particularly also in ventilated patients or in conjunction with ventilating equipment or systems.

The above-mentioned aspects of the present invention and the features and aspects of the invention that are apparent from the further description and claims may be implemented independently of one another and in any desired combinations.

Further advantages, features, properties and aspects of the present invention will become apparent from the claims and the following description of a preferred embodiment by reference to the drawings, wherein:

BRIEF DESCRIPTION OF THE DRAWING

FIG. 14 is a schematic section through the inhalation device during breathing in; and FIG. 15 is a schematic section through a proposed inhalation device according to a third embodiment during breathing in.

DESCRIPTION OF EMBODIMENTS

Figure 1:
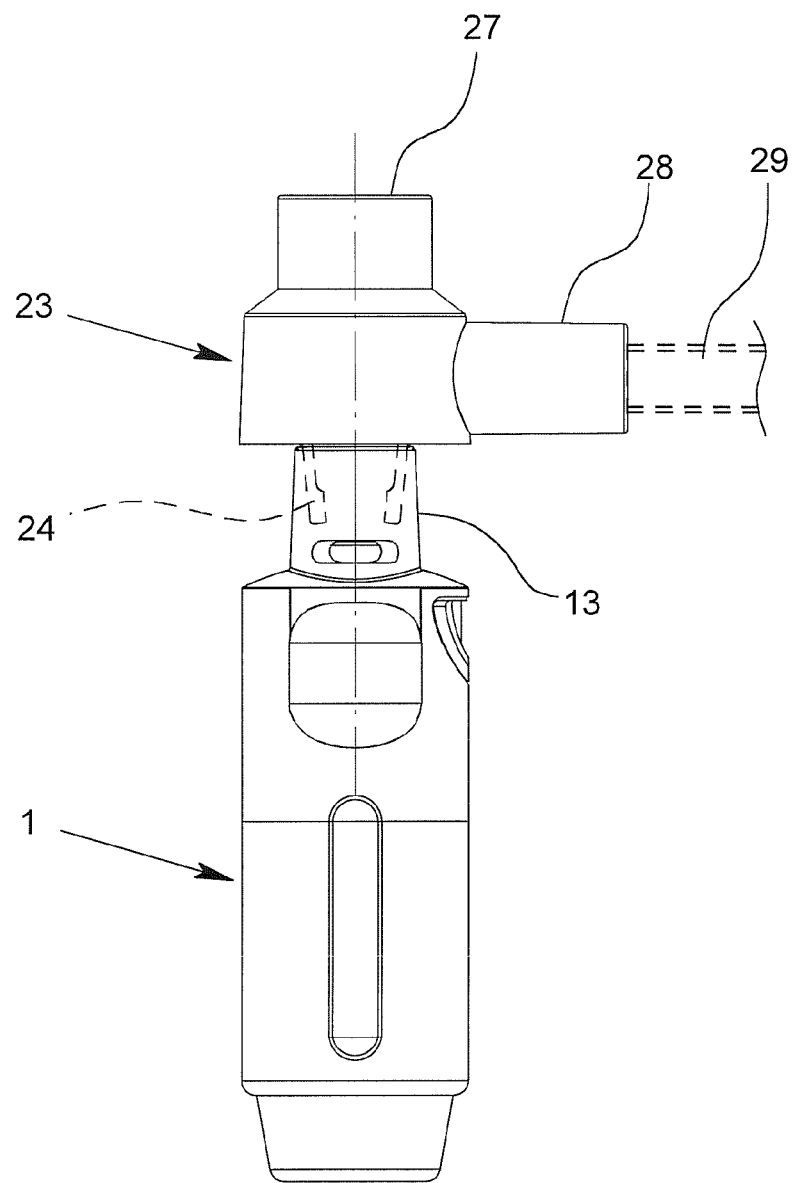
FIG. 1 is a schematic view of a proposed adaptor according to a first embodiment having a nebuliser attached thereto.

In the figures, the same reference numerals have been used for identical or similar parts where corresponding or comparable properties and advantages are achieved, even if the relevant description has not been repeated.

FIG. 1 is a schematic view of a proposed adaptor 23 having an associated nebuliser 1 attached thereto in the drawing.

Figure 2:
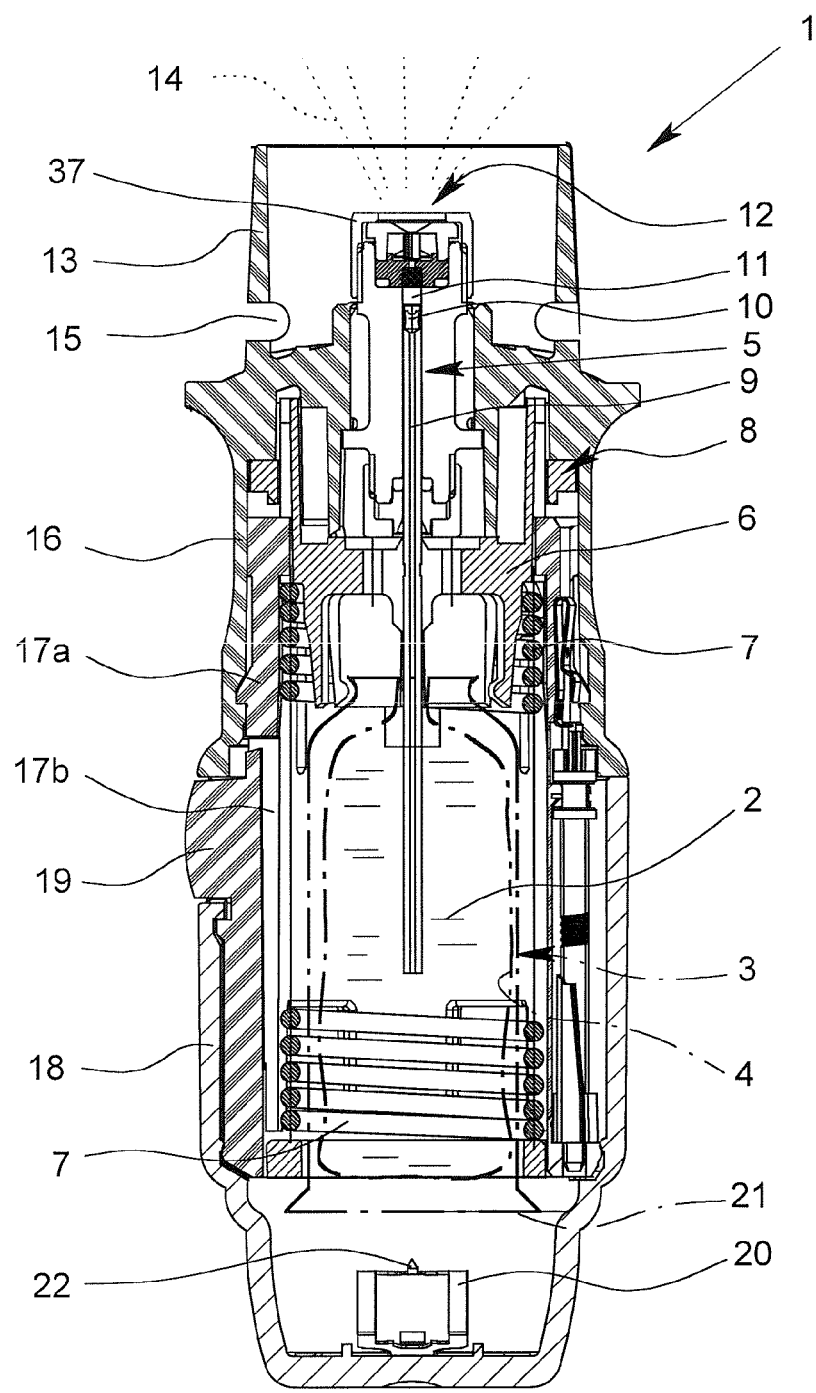
FIG. 2 is a schematic section through a nebuliser in the untensioned state.
Figure 3:
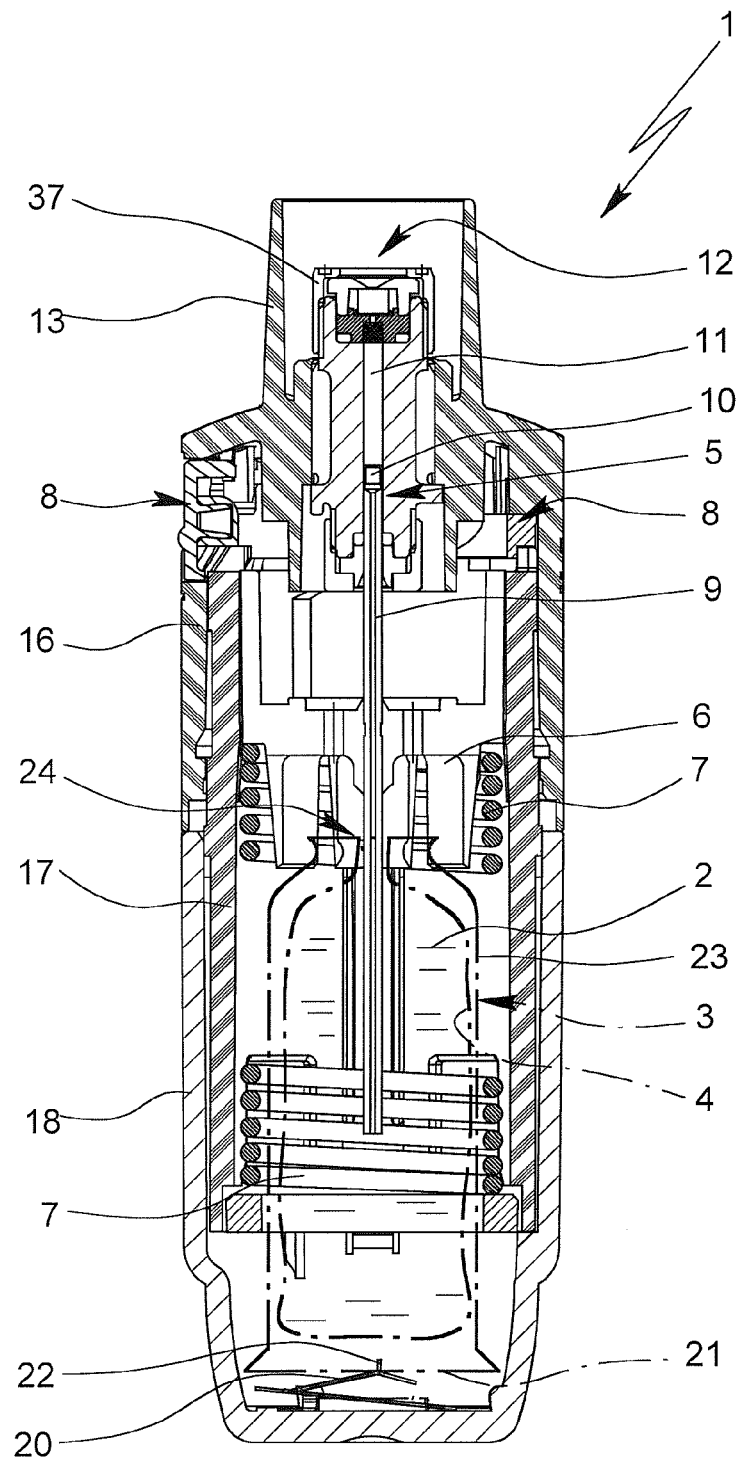
FIG. 3 is a schematic section, rotated through 90° compared with FIG. 2, through the nebuliser in the tensioned state.

FIGS. 2 and 3 show the preferably portable nebuliser 1 for the propellant free nebulisation of a fluid, preferably a liquid or medicament preparation 2 in a schematic view in the untensioned state (FIG. 2) and in the tensioned state (FIG. 3).

FIGS. 2 and 3 show the nebuliser 1 with a container 3 holding the medicament preparation 2.

During the nebulisation of the medicament preparation 2, preferably a liquid, a respirable aerosol 14 (FIG. 2) is formed which can be breathed-in or inhaled by a user or patient (not shown). Normally, inhalation takes place at least once a day, but particularly several times a day, preferably at specified intervals of time, more particularly depending on the complaint suffered by the patient.

The nebuliser 1 comprises the preferably insertable and optionally exchangeable container 3 holding the medicament preparation 2. The container 3 thus forms a reservoir for the medicament preparation 2 which is to be nebulised. Preferably, the container 3 contains a sufficient quantity of medicament preparation 2 or active substance for several doses of the medicament preparation 2, in order to allow a number of nebulisations or applications. A typical container 3 as disclosed in WO 96/06011 A1 holds a volume of about 2 to 10 ml. With regard to the preferred construction of the container 3 reference is additionally made to WO 00/49988 A2.

The container 3 is preferably substantially cylindrical or cartridge-shaped and can be inserted into the nebuliser 1 from below, after it has been opened, and optionally exchanged. It is preferably of rigid construction, the medicament preparation 2 being contained in particular in a collapsible bag 4 in the container 3.

The nebuliser 1 also comprises a conveying device, particularly a pressure generator 5, for conveying and nebulising the medicament preparation 2, particularly in a predetermined and optionally adjustable dosage amount in each case.

The nebuliser 1 or pressure generator 5 comprises in particular a holder 6 for the container 3 and associated drive spring 7 which is only partly shown, preferably having an associated locking element 8 which is manually operable to release it, a conveying element, preferably a conveying tube 9 in the form of a capillary, with an optional valve, particularly a non-return valve 10, a pressure chamber 11 and/or a delivery nozzle 12, particularly in the region of a mouthpiece 13.

The container 3 is fixed in the nebuliser 1 by means of the holder 6, particularly by a clamping or latching action, such that the conveying tube 9 protrudes into the container 3. The holder 6 may be constructed such that the container 3 can be exchanged.

When the drive spring 7 is axially tensioned, the holder 6 with the container 3 and the conveying tube 9 is moved downwards in the figures and the medicament preparation 2—or more precisely the next dose—is sucked out of the container 3 into the pressure chamber 11 of the pressure generator 5 through the non-return valve 10.

During the subsequent release of tension after actuation of the locking element 8, the medicament preparation 2 in the pressure chamber 11 is placed under pressure by moving the conveying tube 9 back up, with the non-return valve 10 now closed, by releasing the tension on the drive spring 7, so that this conveying tube 9 now acts as a pressure ram. This pressure expels the medicament preparation 2 through the delivery nozzle 12, where it is nebulised into the preferably respirable aerosol 14, as shown in FIG. 2.

The user or patient (not shown) can inhale the aerosol 14, while preferably supply air can be sucked into the mouthpiece 13 through at least one supply air opening 15.

During the nebulisation process the container 3 is moved back into its original position by the drive spring 7. The container 3 thus performs a lifting movement during the tensioning process and during the nebulisation process.

The nebuliser 1 comprises in particular a first housing part (upper part) 16 and an inner part 17 which is rotatable relative thereto (FIG. 3) having an upper part 17a and a lower part 17b (FIG. 2), while a second housing part (lower part) 18, which is in particular manually operable or rotatable, is releasably attached, in particular pushed onto the inner part 17, preferably by means of a safety closure or retaining element 19. In particular, the safety closure or retaining element 19 is constructed such that accidental opening of the nebuliser 1 or removal of the second housing part 18 is prevented. In particular, in order to release the second housing part 18, the retaining element 19 has to be pressed in against spring force. In order to insert and/or replace the container 3, the second housing part 18 can be detached from the nebuliser 1. The second housing part 18 preferably forms a cap-like lower housing part and/or engages around or over a lower free end portion of the container 3.

The second housing part 18 can be rotated relative to the first housing part 16, whereby the inner part 17 is also rotated. In this way the drive spring 7 is tensioned in the axial direction by means of a gear (not shown in detail) acting on the holder 6. During tensioning the container 3 is moved axially downwards or with its end portion (further) into the second housing part 18 or towards the end face thereof, until the container 3 assumes an end position shown in FIG. 3. In this state the drive spring 7 or nebuliser 1 is clamped and locked.

The nebuliser 1 preferably has a device for forcibly ventilating the container 3.

When tensioning first takes place, the container 3 is preferably pierced in its base or opened. In particular, an axially acting spring 20 arranged in the housing part 18 comes to abut on the container base 21 and with a piercing element 22 pierces the container 3 or an in particular gas tight seal provided in the base for ventilation purposes when contact is first made.

The device for forcible ventilation is thus formed in this case by the piercing element 22, which is held or formed by the spring 20. However, other design solutions are also possible.

It should be noted that during the piercing for ventilation purposes only the outer shell of the container 3 is opened. The bag 4 containing the medicament preparation 2 remains undamaged. As the medicament formulation 2 is removed from the bag 4 through the conveying tube 9 the flexible bag 4 collapses. For pressure equalisation, ambient air can flow into the container 3 through the ventilation or piercing opening.

In order to use the nebuliser 1, first of all the container 3 has to be inserted. This is preferably done by removing or pulling out the second housing part 18. The container 3 is then axially inserted or pushed into the inner part 17. At the same time the container 3 is opened at the head end or attached. This is done by means of the conveying element, i.e. the conveying tube 9, which pierces a seal preferably provided at the head end of the container 3 and is then inserted through a septum at the head end of the container 3 into the interior of the bag 4. Thus the fluidic connection between the container 3, or more accurately between the bag 4 in the container 3, via the conveying tube 9 to the pressure generator 5 or pressure chamber 11 is produced.

Then the second housing part 18 is pushed on again. The nebuliser 1 can now be tensioned for the first time. At this stage the container 3 is then pierced at its base by the piercing element 22, i.e. forcibly ventilated, as explained previously.

Before being used for the first time and after the container 3 has been inserted and fluidically connected, the nebuliser 1 is preferably tensioned and actuated several times. This so-called priming displaces any air present in the medicament preparation 2 in the conveying tube 9 and in the pressure generator 5 to the delivery nozzle 12. The nebuliser 1 is then ready for inhalation.

The quantity of medicament preparation 2 delivered per spray or nebulisation process is preferably about 10 µl to 50 µl, more particularly about 10 µl to 20 µl, most preferably about 15 µl.

The drive spring 7 is preferably installed in a biased state in order to achieve a high spring pressure. In the proposed nebuliser 1 the pressurisation and conveying of the medicament preparation 2 during the nebulisation process namely takes place preferably only by spring force, and more particularly only by the force of the drive spring 7.

The nebuliser 1 is preferably constructed such that the medicament preparation 2 in the pressure generator 5 or in the pressure chamber 11 reaches a pressure of 5 MPa to 60 MPa, particularly about 10 MPa to 50 MPa during delivery. Particularly preferably, during the delivery or nebulisation of the medicament preparation 2, a pressure of about 5 MPa to 60 MPa, more particularly about 10 to 30 MPa, is reached at the delivery nozzle 12 or at the nozzle openings thereof. The medicament preparation 2 is then converted into the aerosol 14, the droplets of which have an aerodynamic diameter of up to 20 µm, preferably about 3 µm to 10 µm. The nebulising activity or nebulising effect is achieved or further assisted by preferably intercepting jets delivered by the delivery nozzle 12.

The nebuliser 1 is preferably constructed such that the aerosol 14 is delivered at low speed, particularly at a speed of less than 2 m/s, most preferably about 1.6 m/s or less (in each case measured at a distance of 10 cm from the delivery nozzle 12). The nebuliser 1 is thus preferably in the form of a so-called soft mist inhaler. The low delivery speed can be obtained or assisted by intercepting jets of the medicament preparation 2, which are delivered by the delivery nozzle 12 and/or by a suitable choice of spring force.

Particularly preferably, the construction of the nebuliser 1 is such that the aerosol generation lasts for at least 1 s and in particular at least 1.5 s. The time taken to nebulise a dose or to actuate the nebuliser 1 is thus at least 1 s, more particularly more than 1.5 s.

Figure 4:
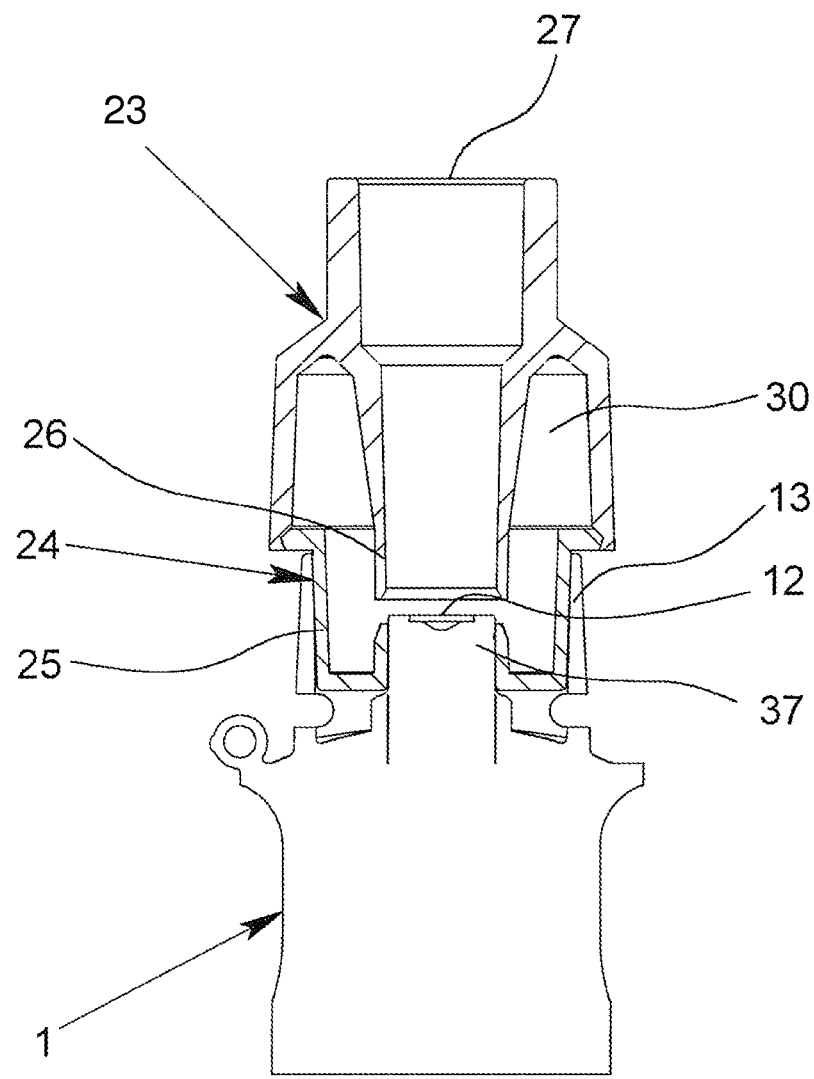
FIG. 4 is a schematic section through the nebuliser with the adaptor attached.
Figure 5:
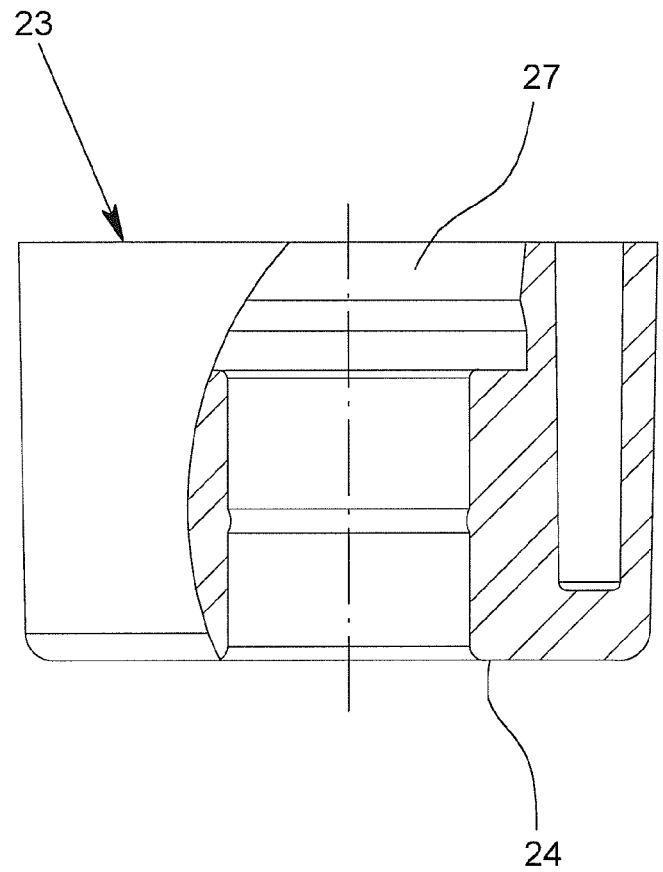
FIG. 5 is a schematic section through a proposed adaptor according to a second embodiment.
Figure 6:
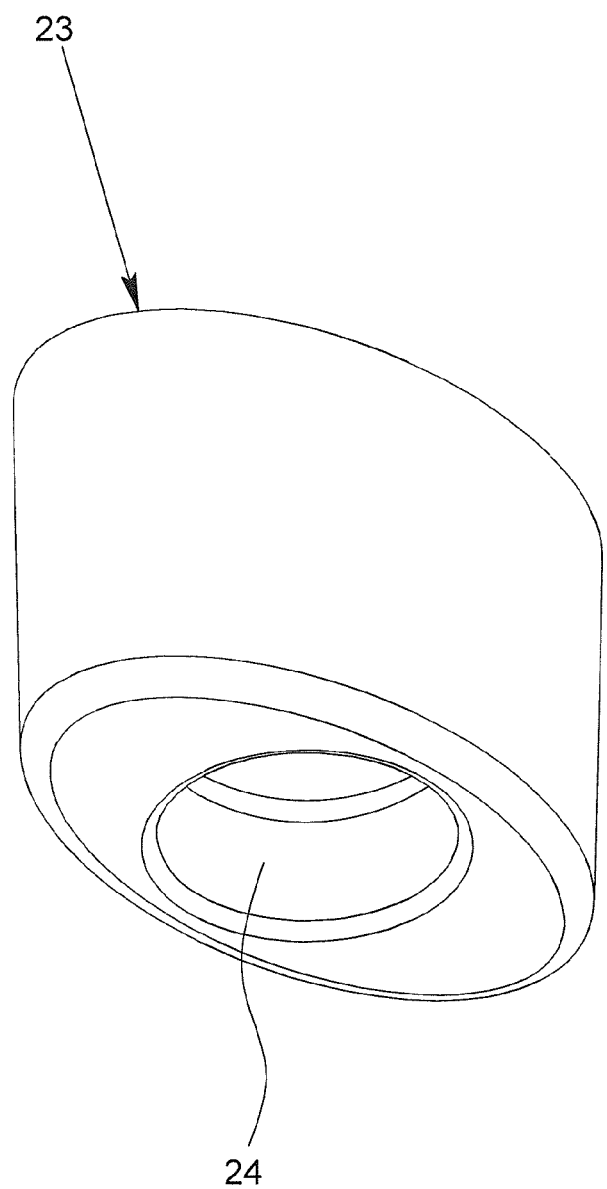
FIG. 6 is a perspective view of the adaptor according to FIG. 5.
Figure 7:
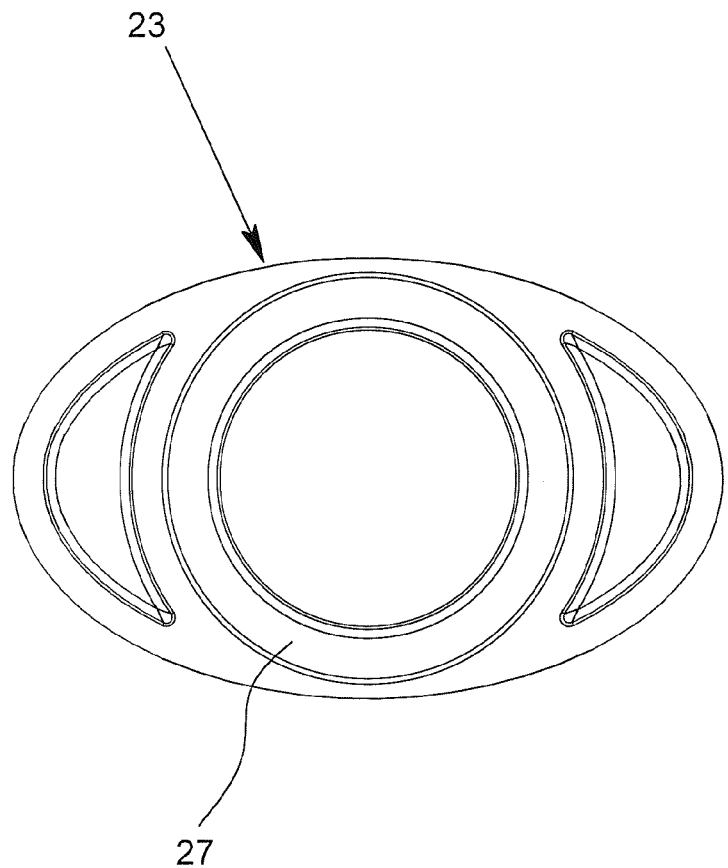
FIG. 7 is a plan view of the adaptor according to FIG. 5.
Figure 8:
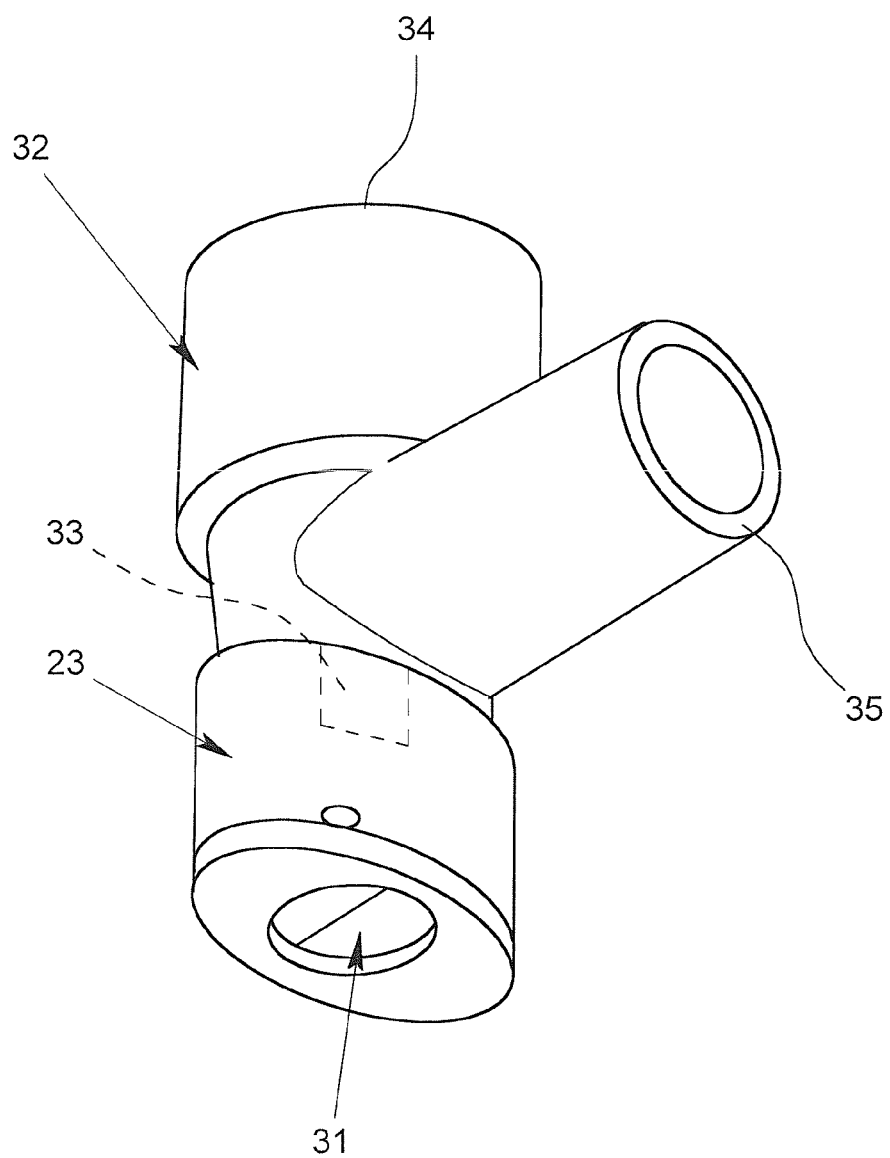
FIG. 8 is a perspective view of a proposed adaptor according to a third embodiment with an attached inhalation device according to a first embodiment.
Figure 9:
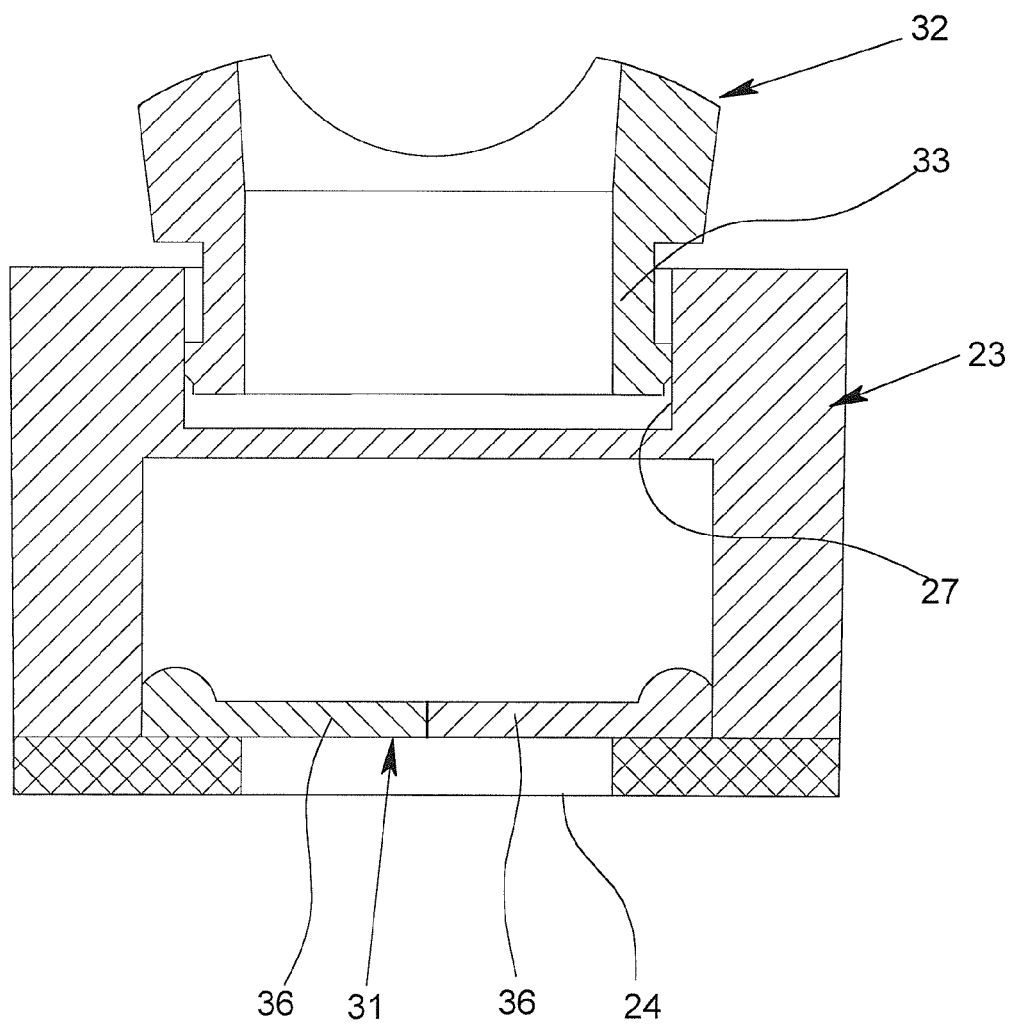
FIG. 9 is sectional representation of an adaptor according to FIG. 8 with no nebuliser attached.

FIG. 4 shows, in schematic section, the adaptor 23 and parts of the attached nebuliser 1, which are shown only schematically.

The adaptor 23 is preferably connected or connectible to the nebuliser 1 or its mouthpiece 13 in releasable and/or more particularly clamping or latching manner.

The adaptor 23 comprises a first connection 24 for the nebuliser 1, more accurately for fluidic and preferably also mechanical connection to the nebuliser 1 or its mouthpiece 13.

In the embodiment shown, the first connection 24 preferably comprises a connecting portion 25 which extends into the mouthpiece 13 and more particularly can be inserted therein. The connecting portion 25 is accordingly adapted in its outer contour to the inner contour of the mouthpiece 13. For example, on its outside, the connecting portion 25 tapers towards the free end and is thus embodied to the at least substantially complementary to a preferably slightly conical shape of the mouthpiece 13. However, other design solutions are also possible.

In the embodiment shown, the first connection 24 or its connecting portion 25 preferably has an oval cross-section for connecting to the preferably oval mouthpiece 13 of the nebuliser 1.

In the embodiment shown the connecting portion 25 preferably closes off a) the substantially annular intermediate space between the expulsion nozzle 12 projecting into the mouthpiece 13 and the inner wall of the mouthpiece 13 with a holder or a projection 37, and/or b) directly closes off the air supply openings 15, particularly so that supply air flows in through the supply air opening or openings 15 only to a lesser extent or not at all into the mouthpiece 13 when the nebuliser 1 or adaptor 23 is used.

The adaptor 23 preferably comprises a connector 26 or other particularly channel-like portion which, when the nebuliser 1 is attached, is associated with the expulsion nozzle 12, particularly covers or receives it or is arranged adjacent thereto, in order to receive or convey onwards the aerosol 14 dispensed by the nebuliser 1 or the expulsion nozzle 12.

In the embodiment shown, the connector 26 terminates at an axial spacing from the expulsion nozzle 12 or a holder associated with the expulsion nozzle 12, so that supply air or breathable air from a ventilation apparatus can flow into the connector 26 (laterally) with the aerosol 14 or flow past the expulsion nozzle 12.

However, it is theoretically also possible for the first connection 24 or connector 26 to be connectible (at least substantially) in leak-tight manner to the expulsion nozzle 12 or a projection 37 that holds or surrounds the expulsion nozzle 12, particularly preferably by fitting on the connector 26, so that no supply air or breathable air can flow past the expulsion nozzle 12 through or into the first connection 24.

The adaptor 23 has a second connection 27 at the patient end. The second connection 27 is preferably in the form of a tube or bore and/or comprises in particular an at least substantially round cross-section.

The second connection 27 is preferably configured for mechanical and/or fluidic connection to a tube, a ventilation apparatus or an inhalation device. However, the second connection 27 may also theoretically be in the form of a mouthpiece.

In the embodiment shown, the adaptor 23 preferably has a third connection 28 shown only in FIG. 1 for supply air or breathable air. The third connection 28 is preferably configured for mechanical and/or fluidic connection to a ventilating tube 29, indicated only by dashed lines, or some other ventilation equipment or the like. For this purpose the third connection 28 is preferably embodied as a connection, tube or pipe, and/or such that the tube 29 or the like can preferably inserted or fitted on.

The present invention preferably relates to use in a ventilated patient or with a ventilator. Accordingly, the term breathable air is generally used hereinafter. The term "breathable air" is preferably to be understood as being a ventilating gas which is provided by a ventilating apparatus or ventilating system for ventilating a patient. Theoretically, the breathable air may also be other supply air and/or exhaled air, particularly when the direction of flow is reversed. The term "breathable air" is therefore preferably to be understood very broadly, so as to cover these alternatives.

The third connection 28 is preferably formed by the adaptor 23 or moulded onto it.

Through the third connection 28, breathable air can preferably be supplied to the first connection 24 or second connection 27 via an annular channel 30 formed by or in the adaptor 23, so that the breathable air can be mixed with the aerosol 14 and/or expelled together with the aerosol 14 through the second connection 27.

In the embodiment shown, the breathable air preferably forms an enveloping current for the aerosol 14 emitted from the expulsion nozzle 12. This is preferably achieved here by guiding the breathable air at least substantially in an annular shape and/or with a twist in the region of the expulsion nozzle 12 and then enabling it to flow through the first connection 24 or connector 26, together with the aerosol 14 (which is not shown in FIG. 4) to the second connection 27. A corresponding fluidic connection is formed for this purpose in the adaptor 23.

The aerosol 14 and the breathable air can then be delivered to the patient (not shown) through the second connection 27, for example by means of a ventilation tube attached thereto, using a face mask or the like.

It should be noted that the third connection 28 is purely optional. Instead of the third connection 28, supply air or breathable air can alternatively be supplied through the supply air opening or openings 15 of the nebuliser 1 or the like.

Further preferred embodiments are explained hereinafter. The previous remarks and explanations apply in a supplementary capacity, in particular, even if the description has not been repeated.

FIG. 5 shows in schematic section a second embodiment of the proposed adaptor 23.

The adaptor 23 is preferably embodied as a disposable item or intended for single use. This makes economic sense because of the particularly simple structure of the adaptor 23 according to the second embodiment, as there is then no need to clean and more particularly sterilise the adaptor 23 after each use.

In the second embodiment the first connection 24 is fluidically connected to the second connection 27 without any branches and more particularly in one piece. In particular, the adaptor 23 does not have a third connection 28. Thus there is no supply of breathable air or supply air at least on the adaptor side.

Preferably, the first connection 24 or the adaptor 23 itself has an oval cross-section, in this case an oval outer contour, for connection to the preferably oval mouthpiece 13 of the nebuliser 1, in this case by insertion in the mouthpiece 13. The preferred oval shape is shown in the perspective view according to FIG. 6 and the plan view according to FIG. 7.

The adaptor 23 is preferably constructed in one piece.

Preferably, the adaptor 23 is embodied as an injection moulded component and/or made of plastics.

In the second embodiment the first and second connections 24, 27 are joined together at least substantially by a preferably straight bore. The first connection 24 comprises a preferably hollow cylindrical inner contour for accommodating the expulsion nozzle 12 or the aerosol 14 emitted therefrom. Particularly preferably, a projection 37 of the nebuliser, which holds or surrounds the expulsion nozzle 12 and is particularly cylindrical, can be inserted in the first connection 24. Thus the expulsion nozzle 12 can be connected in substantially gas-tight manner to the first connection 24. In this case, no supply air can flow through the supply air openings 15 into the first connection 24.

However, it is theoretically also possible for supply air to flow through at least one supply air opening 15 of the nebuliser 1 or the like into the first connection 24 and together with the aerosol 14 to the second connection 27.

The second connection 27 (at the patient end) is preferably embodied as a bushing and/or undercut, so as to be connectable particularly by a latching and/or clamping action to a tube, an inhalation device, a mouthpiece, a face mask or the like. However, other design solutions are also possible.

FIG. 8 shows in perspective view the proposed adaptor 23 according to a third embodiment.

In the third embodiment the adaptor 23 comprises a locking valve 31 which is necessarily open when the adaptor 23 is connected to the nebuliser 1 and is closed when the adaptor 23 is separated from the nebuliser 1. FIG. 9 shows in schematic section the adaptor 23 when the locking valve 31 is closed, i.e. in the state where it is separated from the nebuliser 1. FIG. 10 shows in schematic section the adaptor 23 with the locking valve 31 open, namely in the state in which it is connected to the nebuliser 1.

FIG. 8 shows the adaptor 23 with an inhalation device 32 attached on the outlet side, i.e. to the second connection 27, this device forming an angled piece, in particular.

FIG. 9 shows in schematic section a part of the inhalation device 32, specifically a first port 33 for the nebuliser 1, which can be attached directly via the adaptor 23. Accordingly, the adaptor 23 is connected or connectable by its second connection 27 to the first port 33 of the inhalation device 32, particularly mechanically and/or fluidically. In the embodiment shown the connection 27 and port 33 are connected to one another in particular by a latching or clamping action, in this case by the insertion of the port 33 into the connection 27.

In the embodiment shown the inhalation device 32 is not directly connected to the nebuliser 1 but is connected indirectly via the adaptor 23. This is a preferred embodiment. In particular, the adaptor 23 may be replaceable, particularly preferably if it is releasably connected or connectable to the inhalation device 32.

The inhalation device 32 preferably comprises a second port 34 on the patient side for dispensing breathable air and aerosol 14 (not shown) preferably mixed in via the adaptor 23.

The inhalation device 32 preferably comprises a third port 35 for supplying breathable air, particularly for connection to a tube, not shown here, of a ventilation apparatus or the like (not shown).

Figure 10:
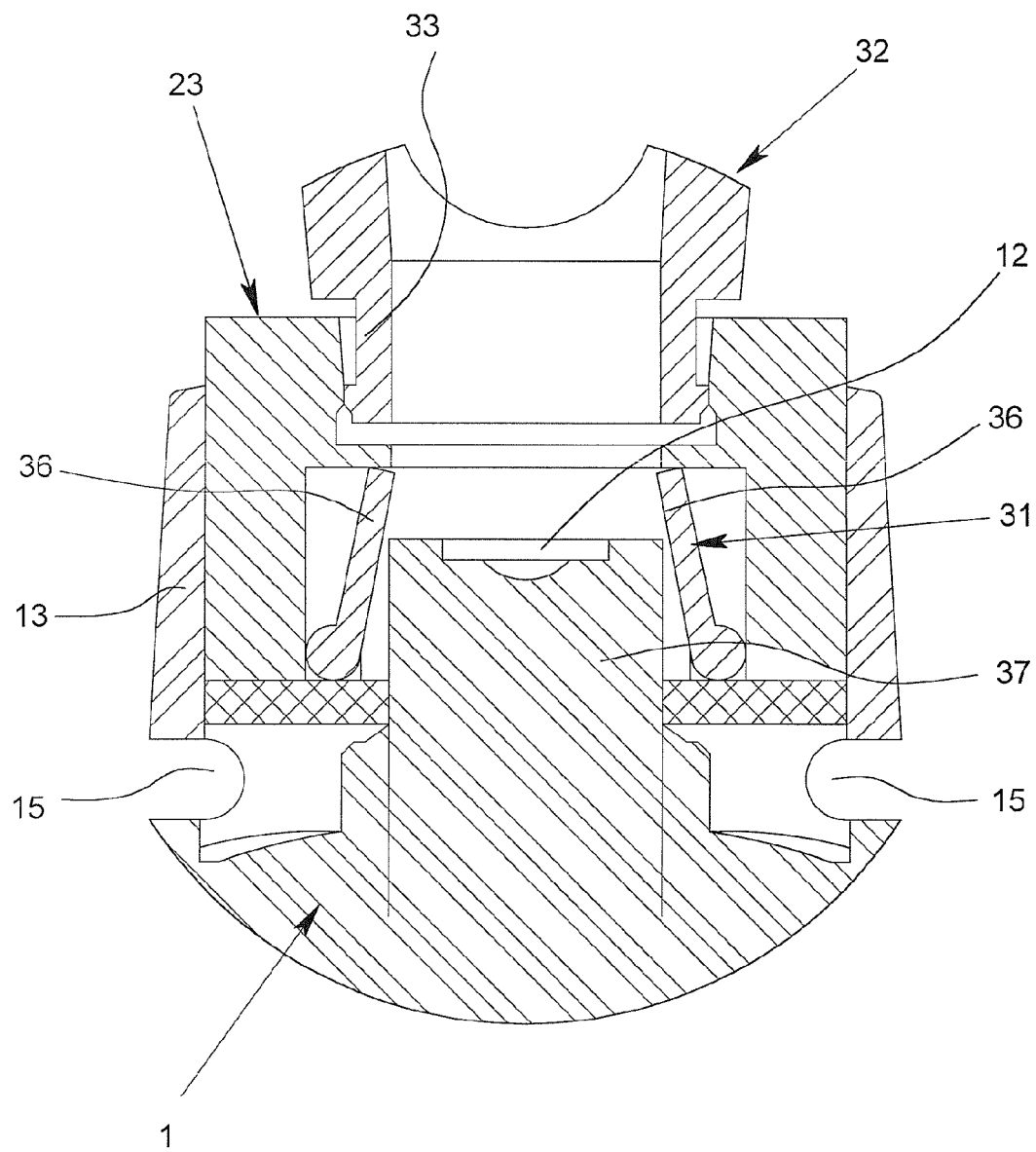
FIG. 10 is a sectional representation of an adaptor according to FIG. 8 with the nebuliser attached.

The schematic section according to FIG. 10 additionally schematically shows a part of the attached nebuliser 1. In the embodiment shown the locking valve 31 comprises at least one, and in this case two, movable valve elements 36 which are opened in particular by the expulsion nozzle 12 or the projection 37 of the nebuliser 1 that holds the expulsion nozzle 12. However, other design solutions are also possible.

The locking valve 31 is preferably biased into the closed position and/or is configured to be self-closing, particularly by means of at least one restoring means (not shown) such as a spring or the like.

When the nebuliser 1 is used, the aerosol 14 produced by the nebuliser 1 is dispensed through the adaptor 23, in this case to the inhalation device 32. From there, the aerosol 14 can be supplied, in particular, together with breathable air, to a patient (not shown) who is being ventilated, in particular. The ventilation is carried out in particular by a corresponding supply of breathable air.

Additional embodiments of the inhalation device 32 are explained hereinafter. The remarks and explanations given previously apply particularly in a supplementary manner, even if the relevant description is not repeated.

Figure 11:
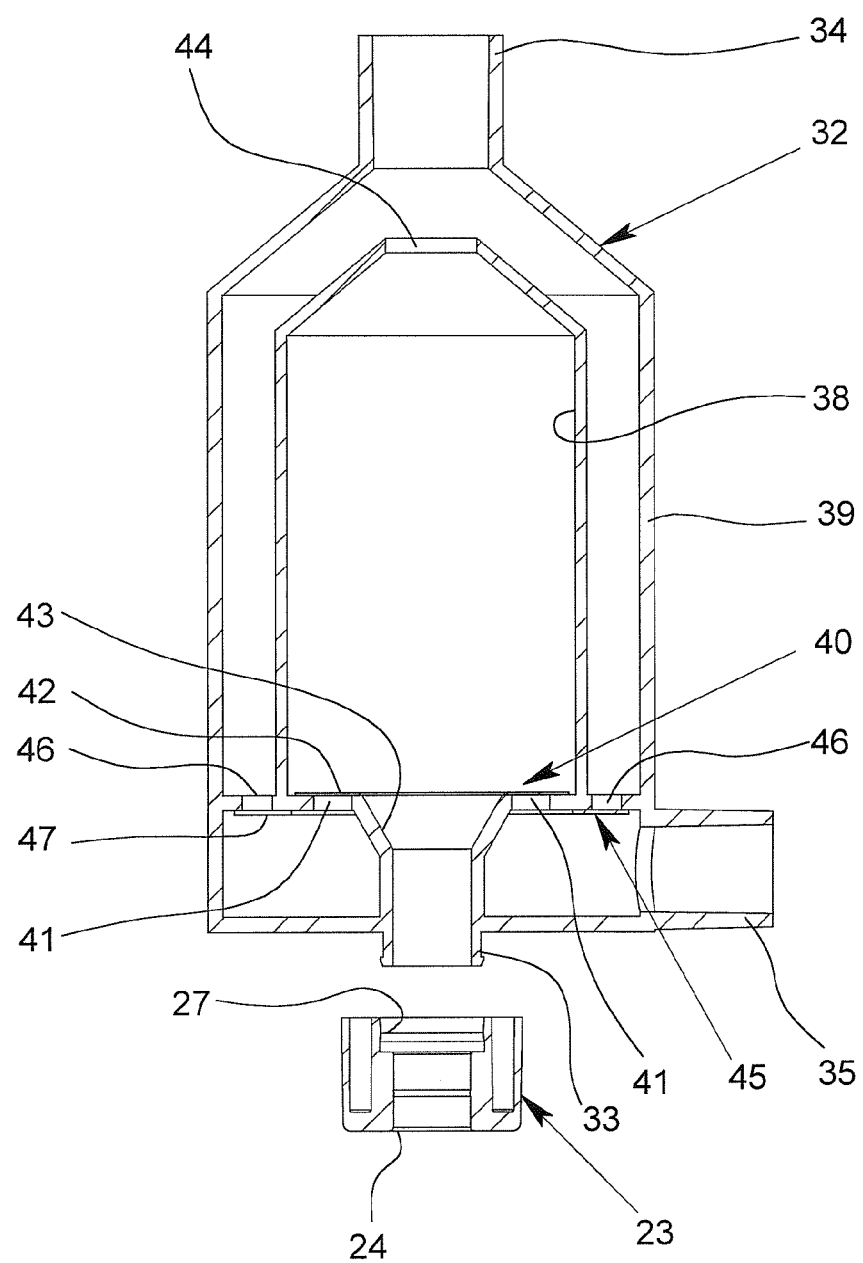
FIG. 11 is a schematic section through a proposed inhalation device according to a second embodiment with an associated adaptor.

FIG. 11 is a schematic sectional representation of the proposed inhalation device 32 according to a second embodiment.

As in the previous embodiment the inhalation device 32 may be attached to the nebuliser 1 via the adaptor 23. However, the first port 33 of the inhalation device 32 may also be configured for direct connection to the nebuliser 1 or mouthpiece 13. If desired, the adaptor 23 or the optional locking valve 31 thereof may also be integrated in the inhalation device 32 or its port 33. In particular, the first port 33 of the inhalation device 32 is then configured for fluidic and/or mechanical connection to the nebuliser 1 or its mouthpiece 13.

The inhalation device 32 preferably comprises a chamber 38 for the intermediate storage of the aerosol 14 (not shown) produced by the nebuliser 1. In particular, this is an inner chamber which is arranged within a housing 39 of the inhalation device 32.

The chamber 38 is fluidically connected to the first port 33 preferably directly, more particularly without a valve, especially so that at least when the nebuliser 1 is attached the aerosol 14 produced by the nebuliser 1 can flow into the chamber 38 in valve-free and if possible without any wastage. If the locking valve 31 is provided, this is open when the nebuliser 1 is attached and thus does not constitute a valve that has to be opened by the aerosol 14, or an obstacle to be overcome.

By the term "free from wastage" is meant in particular, in the present invention, that unwanted precipitation of the aerosol 14 or of the nebulised fluid is substantially prevented or at least minimised.

The chamber 38 is connected on the inlet side not only to the first port 33 but preferably in parallel on the inlet side to the third port 35 of the inhalation device 32, via an inlet valve 40, so that breathable air can flow from the third port 35 into the chamber 38 or through the chamber 38, particularly at least substantially parallel to the main direction of the flow of the aerosol 14.

Figure 12:
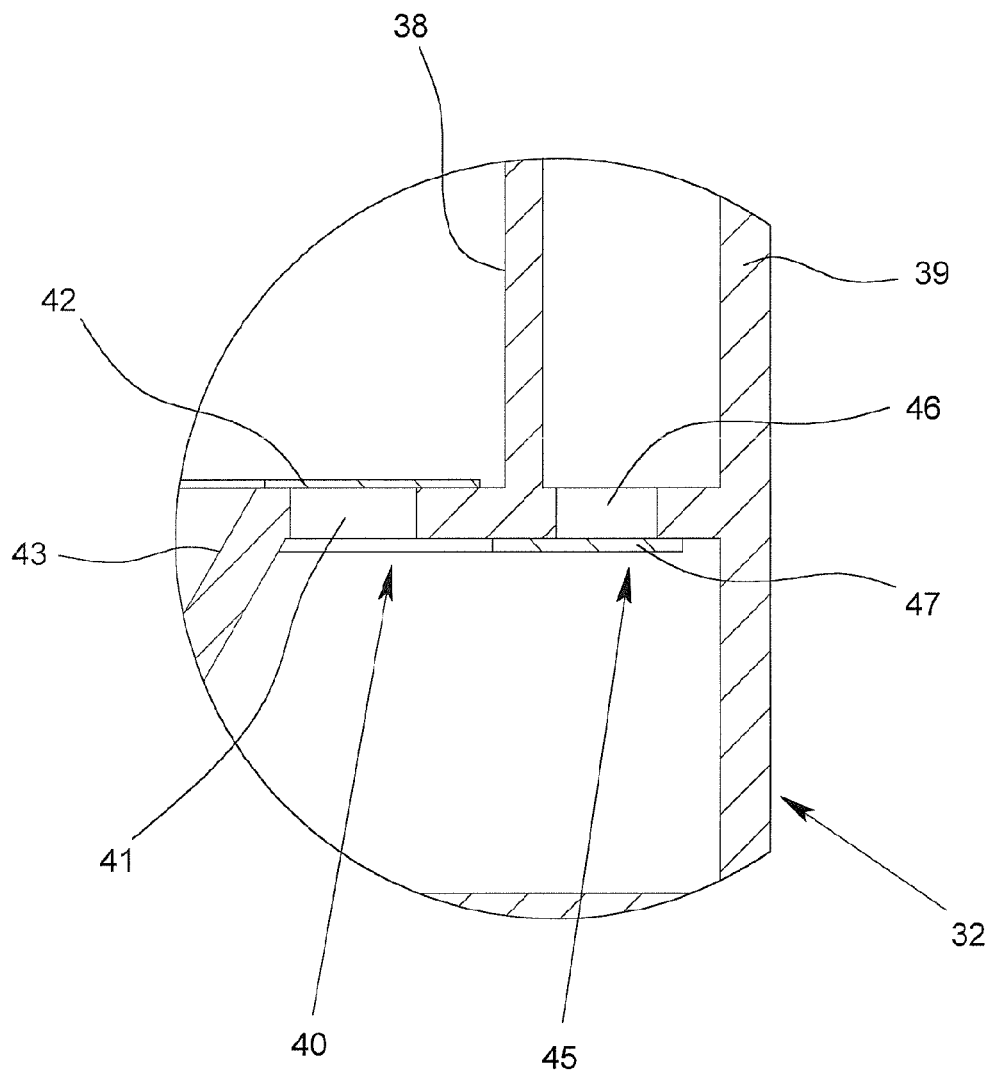
FIG. 12 is a magnification of a detail from FIG. 11.

The inlet valve 40 is schematically shown in FIG. 11 and in the detailed magnification of FIG. 11 shown in FIG. 12. In particular, it is a one-way or non-return valve. The inlet valve 40 is preferably configured to be self-closing and/or (slightly) biased into the closed position.

In the embodiment shown, the inlet valve 40 preferably comprises a plurality of inlet openings 41 which can be covered or closed off in particular by a common valve element 42, or a plurality of separate valve elements 42.

The inlet openings 41 are preferably arranged about a central or middle connecting channel 43 which connects the first port 33 to the chamber 38. However, other design solutions or arrangements are also possible.

On the outlet side the chamber 38 is preferably fluidically connected to the second port 34 of the inhalation device 32 in valve-free manner.

In the embodiment shown, the chamber 38 comprises a preferably central outlet opening 44 to which the second port 34 is attached, preferably on a straight extension of the main direction of flow of the aerosol 14 which is preferably at least substantially straight. However, other design solutions are also possible.

The inhalation device 32 preferably comprises an outlet valve 45 via which the second port 34 is attached to the third port 35 parallel to the chamber 38 such that breathable air can flow from the second port 34 past the chamber 38 through the outlet valve 45 to the third port 35. In particular, a flow path—in this embodiment and intermediate or annular—is formed between the chamber 38 or a preferably substantially cylindrical wall that forms the chamber 38, on the one hand, and the housing 39, on the other hand, said intermediate or annular chamber allowing the breathable air to flow from the second port 34 through the outlet valve 45 to the third port 35.

The outlet valve 45 preferably comprises a plurality of valve openings 46 arranged particularly in a ring around a periphery of the intermediate chamber or annular chamber, which can be closed off by a common or a plurality of separate valve elements 47, in the embodiment shown.

The outlet valve 45 is preferably in the form of a one-way or non-return valve.

The outlet valve 45 or its valve element 47 is preferably embodied to be self-closing and/or (slightly) biased into the closed position.

The valve element 42 and/or 47 is preferably configured in one piece and/or may be deformed by elastic deformation from the closed position into an open position. However, other design solutions are also possible.

The outlet valve 45 is preferably arranged concentrically with the inlet valve 40 and/or adjacent to the inlet valve and/or arranged around the inlet valve 40. However, other design solutions or arrangements are also possible.

The inlet valve 40 and/or outlet valve 45 is preferably arranged in the region of the inlet of the chamber 38 or adjacent to the connecting channel 43.

Figure 13:
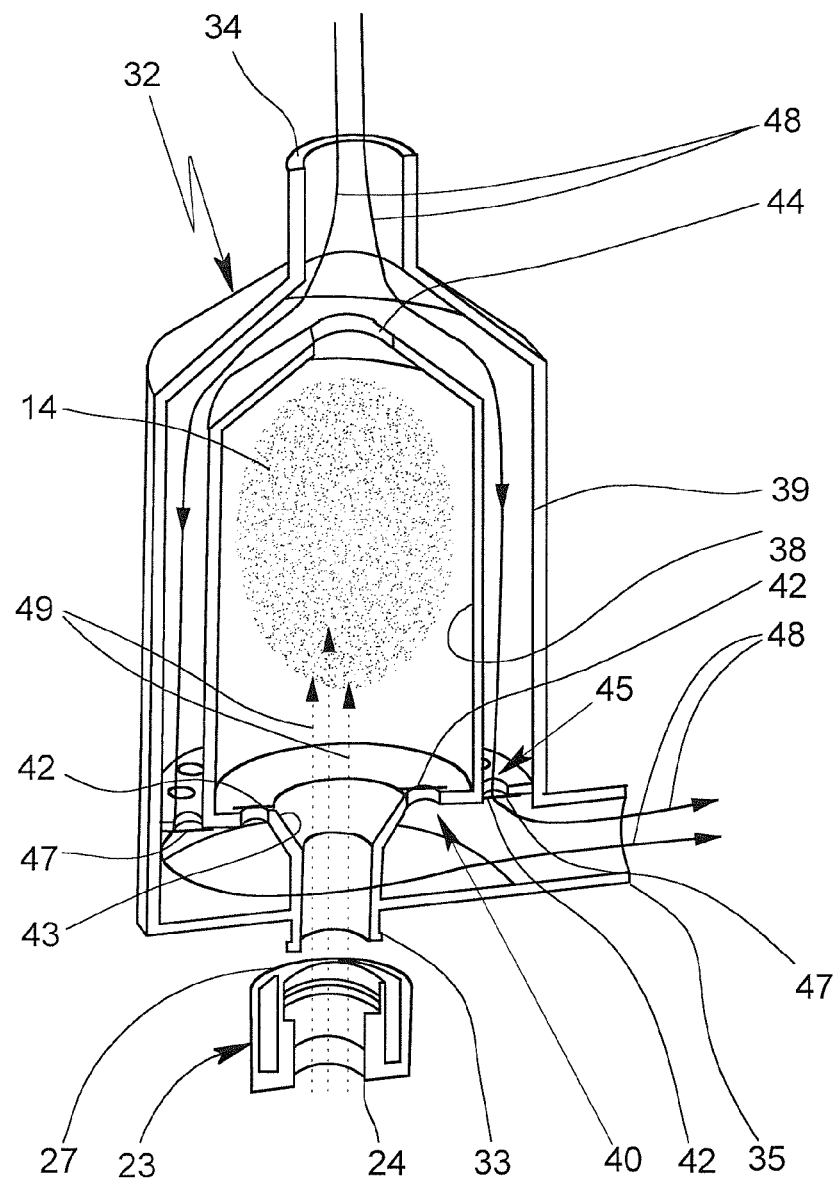
FIG. 13 is a schematic section through the inhalation device during breathing out.

FIG. 13 shows in a schematic sectional representation the air flow when breathing out. The breathed-out air 48 can flow into the inhalation device 32 through the second port 34 and from there past the chamber 38 or around the chamber 38 through the outlet valve 45, which opens automatically, to the third port 35 and from this it can flow out of the inhalation device 32, as indicated by arrows 48. This breathed-out air 48 cannot flow into the chamber 38 as the inlet valve 40 is closed in this direction or closes automatically.

FIG. 13 schematically shows, by means of dashed arrows 49, how the aerosol 14 can flow, optionally simultaneously or in parallel or independently thereof, from the nebuliser 1 (not shown) through the optional adaptor 23, the first port 33 and the connecting channel 43 into the chamber 38 where it forms an aerosol mist 14. This aerosol mist is not affected by the breathed-out air 48.

Figure 14:
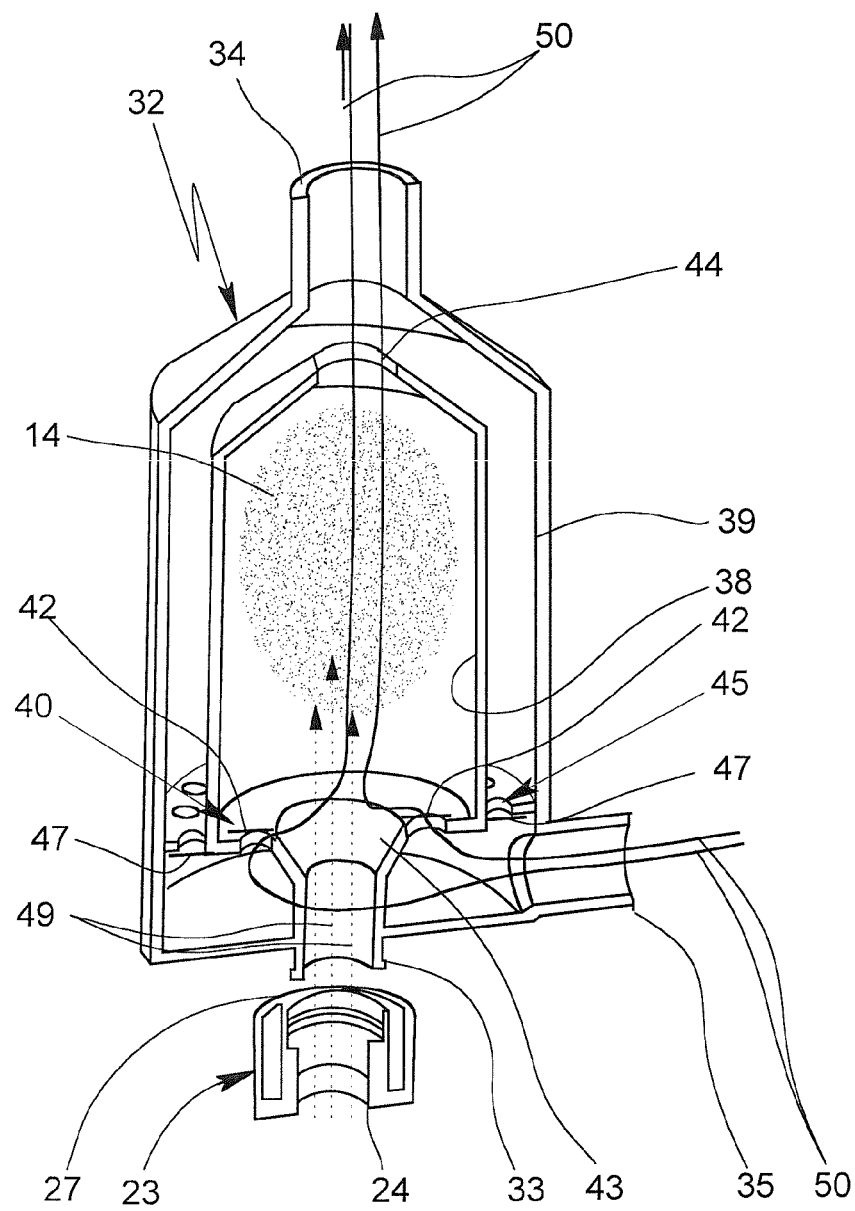

FIG. 14 shows the situation when breathing in, i.e. when breathable air flows through the third port 35 into the inhalation device 32 and is delivered through the second port 34 to the patient (not shown), particularly through a tube, face mask, other ventilation device or a mouthpiece or the like (not shown) to the patient (not shown). The thus breathed-in air is indicated by arrows 50 in FIG. 14. The breathed-in air 50 flows through the inlet valve 40 which opens automatically in this direction, into the chamber 38 on the inlet side, and flows together with the aerosol 14 which is carried along in particular by the breathed-in air 50, through the preferably constantly open outlet opening 44 of the chamber 38 and onto the second port 34, i.e. out of the inhalation device 32. The breathed-in air 50 cannot flow around the chamber 38 through the outlet valve 45 as the outlet valve 45 is closed or closes automatically in this direction.

Figure 15:
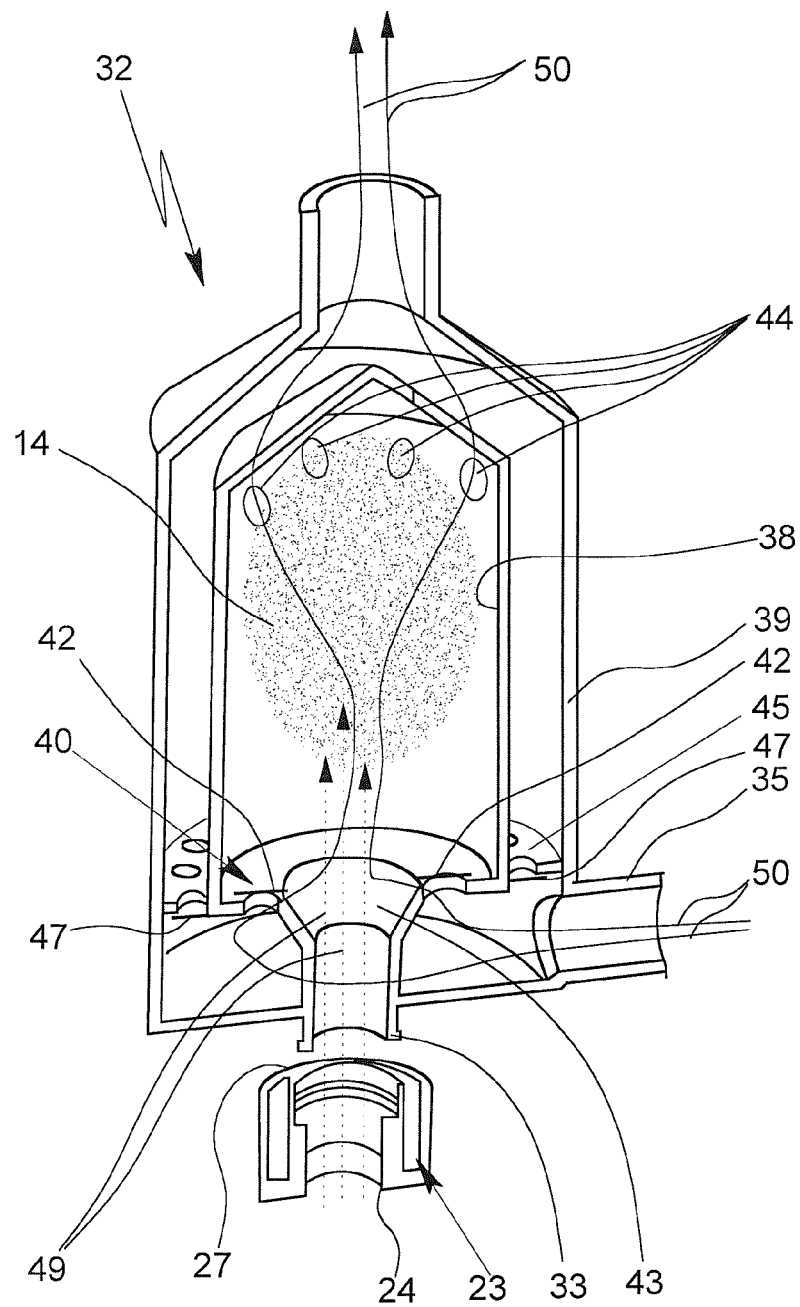

FIG. 15 shows a second embodiment of the proposed inhalation device 32, in a view corresponding to FIG. 14, during breathing in, i.e. during the supplying of breathable air to a patient (not shown). In contrast to the first embodiment the inhalation device 32 according to the second embodiment comprises a plurality of outlet openings 44 at the chamber 38 which are arranged in particular in an annular arrangement and/or concentrically with respect to the preferably central second port 34 (the second port 34 adjoins the annular arrangement of the outlet openings 44 particularly axially or downstream). Tests have shown that, surprisingly, this results in a dispensing of the aerosol 14 free from wastage while ensuring thorough mixing with the breathed-in air 50 which is supplied or sucked in.

It should be noted that the inlet valve 40 is preferably configured such that its valve element 42 opens towards the centre or towards the connecting channel 43 or the free end or free edge points towards the centre. In particular, this or another configuration ensures that breathed-in air 50 flowing into the chamber 38 flows in adjacent to the end of the connecting channel 43 in order to produce an additional Venturi effect, if required. However, other design solutions are also possible.

Generally speaking, it should be noted that the individual embodiments and alternatives and the respective features and aspects may be combined with one another in any desired manner but may also be implemented of one another.

The present invention proposes in particular a combination of the nebuliser 1 described above or some other nebuliser 1 with the adaptor 23 and the inhalation device 32. However, the adaptor 23 and the inhalation device 32 may also be used independently of one another in conjunction with the nebuliser 1 or with other nebulisers 1.

Furthermore, the present invention is directed to using the adaptor 23 and/or the inhalation device 32 with a ventilating apparatus or for ventilating a patient. However, the inhalation device 32 may also, in particular, be used for other purposes, for example as a so-called spacer. In this case the third port 35 can be omitted or it may be connected to the nebuliser 1. If necessary the breathable air or supply air can then be supplied through at least one supply air opening 15 of the nebuliser 1 or by some other method. Alternatively, the third port 35 may be used only for admitting breathed-out air 48.

To complete the disclosure of the present application and with regard to the preferred embodiment of the nebuliser 1, reference is hereby made, in precautionary manner, to the total disclosure of both WO 91/14468 A1 and also WO 97/12687 A1.

In contrast to free-standing appliances or the like, the proposed nebuliser 1 is preferably designed to be portable and in particular is a mobile hand-held device.

By virtue of its cylindrical shape and handy size of less than 9 to 15 cm long and 2 to 4 cm wide, the nebuliser 1 can be carried by the patient at all times. The nebuliser sprays a defined volume of the medicament preparation 2 by the application of high pressures through small nozzles, so as to form inhalable aerosols 14.

The nebuliser 1 operates purely mechanically, in particular. However, the nebuliser 1 may theoretically operate by any other method. In particular, the expression "conveying device" or "pressure generator" must be understood in very general terms. For example, the pressure required for the delivery and nebulisation may also be generated by propellant gas, a pump or by any other suitable method.

The nebuliser 1 is designed in particular for the brief nebulisation of the medicament preparation 2, for example for one to two breaths. However, it may also be designed or used for longer or continuous nebulisation.

Some preferred ingredients, compounds and/or formulations of the fluid or the medicament preparation 2 are listed below.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1 dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3.4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

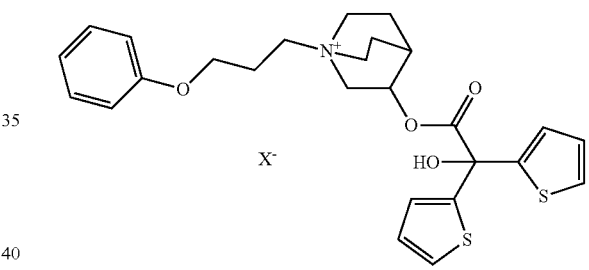

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

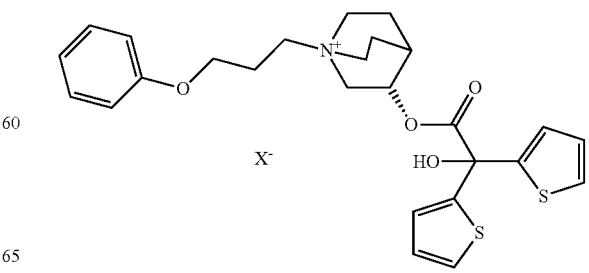

AC-1-en wherein X⁻ may have the above-mentioned meanings. Other preferred anticholinergics are selected from the salts of formula AC-2

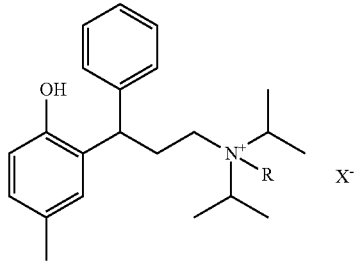

AC-2 wherein R denotes either methyl or ethyl and wherein X⁻ may have the above-mentioned meanings. In an alternative embodiment the compound of formula AC-2 may also be present in the form of the free base AC-2-base.

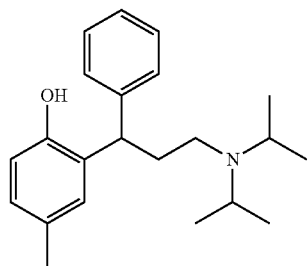

AC-2-base

Other specified compounds are:
tropenol 2,2-diphenylpropionate methobromide;
scopine 2,2-diphenylpropionate methobromide;
scopine 2-fluoro-2,2-diphenylacetate methobromide;
tropenol 2-fluoro-2,2-diphenylacetate methobromide;
tropenol 3,3',4,4'-tetrafluorobenzilate methobromide;
scopine 3,3',4,4'-tetrafluorobenzilate methobromide;
tropenol 4,4'-difluorobenzilate methobromide;
scopine 4,4'-difluorobenzilate methobromide;
tropenol 3,3'-difluorobenzilate methobromide;
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the metho-X salts are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1 (R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylaminoethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy)-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| | List of reference numerals |
|---|---|
| 1 | nebuliser |
| 2 | medicament preparation |
| 3 | container |
| 4 | bag |
| 5 | pressure generator |
| 6 | holder |
| 7 | drive spring |
| 8 | locking element |
| 9 | conveying tube |
| 10 | non-return valve |
| 11 | pressure chamber |
| 12 | expulsion nozzle |
| 13 | mouthpiece |
| 14 | aerosol |
| 15 | supply air opening |
| 16 | first housing part (upper part) |
| 17 | inner part |
| 17a | upper part of the inner part |
| 17b | lower part of the inner part |
| 18 | second housing part (lower part) |
| 19 | retaining element |
| 20 | spring (in the lower housing part) |
| 21 | container base |
| 22 | piercing element |
| 23 | adapter |
| 24 | first connection (adapter) |
| 25 | connecting portion |
| 26 | connector |
| 27 | second connection (adapter) |
| 28 | third connection (adapter) |
| 29 | tube |
| 30 | annular channel |
| 31 | locking valve |
| 32 | inhalation device |
| 33 | first connection (inhalation device) |
| 34 | second connection (inhalation device) |
| 35 | third connection (inhalation device) |
| 36 | valve element |
| 37 | projection |
| 38 | chamber |
| 39 | housing |
| 40 | inlet valve |
| 41 | inlet opening |
| 42 | valve element |
| 43 | connecting channel |
| 44 | outlet opening |
| 45 | outlet valve |
| 46 | valve opening |
| 47 | valve element |
| 48 | breathed out air |
| 49 | aerosol flow |
| 50 | breathed in air |

The invention claimed is:

1. An adapter (23), comprising:
a first connection (24) configured to connect to a mouthpiece of a nebuliser (1),
a second connection (27) configured to receive an aerosol (14) and to deliver the aerosol (14) to a patient,
a third connection (28) configured to receive breathable air from a source,
a connector (26) configured to be in fluidic association with an expulsion nozzle (12) of the nebuliser (1) when the first connection (24) is connected to the nebulizer (1), the connector (26) being configured to receive the aerosol (14) dispensed from the expulsion nozzle (12) and convey the aerosol (14) to the second connection (27),
wherein the first connection (24) is connectible in a substantially leak-tight manner to at least one of the expulsion nozzle (12) and a projection (37) that surrounds the expulsion nozzle (12), so that no supply air or breathable air can flow past the expulsion nozzle (12) through or into the first connection (24), thereby closing off air supply openings (15) of the nebulizer (1).

2. The adapter according to claim 1, wherein the second connection (27) has a round cross-section.

3. The adapter according to claim 1, wherein the second connection (27) is configured for connection to a tube (29) or an inhalation device (32).

4. The Adapter according to claim 1, wherein the adapter (23) is configured in one piece and in the form of an injection moulding.

5. The Adapter according to claim 1, wherein the adapter (23) comprises a locking valve (31) which automatically opens when the adapter (23) is connected to the nebuliser (1) and closes when the adapter (23) is separated from the nebuliser (1).

6. The Adapter (23) according to claim 5, wherein the locking valve (31) comprises at least one movable valve element (36) which is opened by the expulsion nozzle (12) or by the projection (37).

7. The Adapter (23) according to claim 6, wherein the locking valve (31) is biased into the closed position and/or is configured to be self-closing.

8. The Adapter (23) according to claim 6, wherein, when the nebuliser (1) is attached to the adapter (23), the at least one movable valve element (36) is sidewise of the expulsion nozzle (12) or of the projection (37) that holds or surrounds the expulsion nozzle (12).

9. The Adapter according to claim 1, wherein the third connection (28) is for connection to a tube (29) or a ventilator.

10. The adaptor (23) according to claim 1, wherein the first connection (24) comprises a connecting portion (25) having an outer contour inserted within, and in engagement with, an inner wall of the mouthpiece (13) of the nebuliser (1), the connecting portion (25) extending into the mouthpiece (13) when the adapter (23) is connected to the nebulizer (1).

11. The adapter (23) according to claim 10, wherein, when the adapter (23) is connected to the nebulizer (1), the connecting portion (25) closes off a substantially annular intermediate space between the expulsion nozzle (12) projecting into the mouthpiece (13) with the projection (37), and the inner wall of the mouthpiece (13), and closes off air supply openings (15) of the nebulizer (1), so that no supply air flows in through the supply air opening or openings (15) into the mouthpiece (13) when the adaptor (23) is used.

12. The adapter (23) according to claim 1, wherein the first connection (24) has an oval cross-section for connection to the mouthpiece (13) of the nebuliser (1), which is also oval.

13. The adapter (23) according to claim 1, wherein the first and second connections (24, 27) are fluidically connected to one another without branching.

14. The adapter according to claim 1, wherein through the third connection (28), breathable air is supplied to at least one of the first connection (24) and the second connection (27) via an annular channel (30) formed in the adaptor (23), so that the breathable air is mixed with aerosol (14) from the nebulizer (1) and expelled together with the aerosol (14) through the second connection (27).

15. The adapter according to claim 14, wherein the breathable air is enabled to flow at least substantially in an annular shape and/or with a twist in the region of the expulsion nozzle (12) and then through the first connection (24), together with the aerosol (14) to the second connection (27).

16. An apparatus, comprising:
a nebulizer (1) having an expulsion nozzle (12) and a projection supporting the nozzle (12); and
an adapter (23) releasable connectable to the nebulizer (1), wherein said adapter (23) includes:
a connection (24) configured to connect to a mouthpiece of the nebuliser (1),
a connector (26) configured such that the connector (26) is in fluidic association with the expulsion nozzle (12) of the nebuliser (1) when the adapter (23) is connected to the nebuliser (1), the connector (26) being configured to receive an aerosol (14) dispensed from the expulsion nozzle (12) and convey the aerosol toward a patient side of the adapter (23),
a locking valve (31) which automatically opens when the adapter (23) is connected to the nebuliser (1) and closes when the adapter (23) is separated from the nebuliser (1), where the locking valve (31) comprises at least one movable valve element (36) which is opened by the expulsion nozzle (12) or a projection (37),
wherein the connection (24) is connectible in a substantially leak-tight manner to at least one of the expulsion nozzle (12) and the projection (37) that surrounds the expulsion nozzle (12), so that no supply air or breathable air can flow past the expulsion nozzle (12) through or into the connection (24), and wherein the connector (26) terminates at an axial spacing from the expulsion nozzle (12) so that supply air or breathable air from another connection (28) can flow into the connector (26) with the aerosol (14) or flow past the expulsion nozzle (12).

17. An Adapter (23), comprising:
a first connection (24) configured to connect to a nebuliser (1), wherein the nebulizer (1) comprises a mouthpiece (13), an expulsion nozzle (12) projecting into the mouthpiece (13), and a substantially annular intermediate space between the expulsion nozzle (12) and an inner wall of the mouthpiece (13),
a second connection (27) configured to receive an aerosol (14) from the nebulizer (1) and to deliver the aerosol (14) to a patient,
a third connection (28) configured to receive breathable air from a source,
a connector (26) configured such that the connector (26) is in fluidic association with the expulsion nozzle (12) of the nebuliser (1) when the first connection (24) is connected to the nebuliser (1), the connector (26) being configured to receive the aerosol (14) dispensed from the expulsion nozzle (12) and convey the aerosol (14) to the second connection (27),
wherein the first connection (24) is connectible in a substantially leak-tight manner to at least one of the expulsion nozzle (12) and a projection (37) that surrounds the expulsion nozzle (12), so that no supply air or breathable air can flow past the expulsion nozzle (12) through or into the first connection (24), and
wherein the first connection (24) comprises an annular connecting portion (25) that is surrounded by, fills, and closes off the substantially annular intermediate space.

18. The Adapter according to claim 17, wherein the first connection (24) and the second connection (27) are joined together at least substantially by a straight bore.

19. An Adapter (23), comprising:
a first connection (24) configured to connect to a mouthpiece of a nebuliser (1),
a second connection (27) configured to receive an aerosol (14) from the nebulizer (1) and to deliver the aerosol (14) to a patient,
a third connection (28) configured to receive breathable air from a source, a connector (26) located between the first and second connection such that the connector (26) is in fluidic association with an expulsion nozzle (12) of the nebuliser (1) when the first connection (24) is connected to the nebulizer (1), wherein the connector (26) terminates at an axial spacing from the expulsion nozzle (12) so that the breathable air from the third connection (28) flows past the expulsion nozzle (12) and into the connector (26) with the aerosol (14), the connector (26) being configured to convey the aerosol (14) to the second connection (27), wherein the first connection (24) is connectible in a substantially leak-tight manner to at least one of the expulsion nozzle (12) and a projection (37) that surrounds the expulsion nozzle (12) so that no supply air or breathable air can flow past the expulsion nozzle (12) through or into the first connection (24), and the first connection (24), the second connection (27), and the connector (26) each include a respective longitudinal axis, which are axially aligned, and are in fluidic communication via a straight bore along the respective longitudinal axes.

20. The Adapter according to claim 19, further comprising an annular channel (30) about the connector (26) and configured to receive the breathable air from the third connection (28) and convey the breathable air to at least one of the first connection (24) and the second connection (27), so that the breathable air at least one of mixes and is expelled with the aerosol (14) through the second connection (27).

21. The Adapter according to claim 19, further comprising a fluidic passage configured to guide the breathable air from the third connection (28) at least substantially in an annular shape and/or with a twist in a region of the expulsion nozzle (12), and such that the breathable air forms an enveloping current for the aerosol (14) emitted from the expulsion nozzle (12), thereby enabling the breathable air to flow through the connector (26), together with the aerosol (14) to the second connection (27).

* * * * *